US008871956B2

(12) United States Patent
Bailly et al.

(10) Patent No.: US 8,871,956 B2
(45) Date of Patent: Oct. 28, 2014

(54) METHOD FOR PREPARING 3-KETO-BENZOFURANE DERIVATIVES

(75) Inventors: Fréderic Bailly, Paris (FR); Thomas Priem, Paris (FR); Philippe Vayron, Paris (FR)

(73) Assignee: Sanofi, Paris (FR)

( * ) Notice: Subject to any disclaimer, the term of this patent is extended or adjusted under 35 U.S.C. 154(b) by 60 days.

(21) Appl. No.: 13/638,484

(22) PCT Filed: Mar. 30, 2011

(86) PCT No.: PCT/FR2011/050706
§ 371 (c)(1),
(2), (4) Date: Feb. 26, 2013

(87) PCT Pub. No.: WO2011/131881
PCT Pub. Date: Oct. 27, 2011

(65) Prior Publication Data
US 2013/0165673 A1    Jun. 27, 2013

(30) Foreign Application Priority Data

Mar. 30, 2010 (FR) ..................... 10 52332

(51) Int. Cl.
*C07D 307/00* (2006.01)
*C07D 307/81* (2006.01)
*C07D 307/80* (2006.01)
*C07D 307/79* (2006.01)

(52) U.S. Cl.
CPC ............ *C07D 307/81* (2013.01); *C07D 307/80* (2013.01); *C07D 307/79* (2013.01)
USPC ...................................................... 549/468

(58) Field of Classification Search
USPC ........................................................ 549/468
See application file for complete search history.

(56) References Cited

FOREIGN PATENT DOCUMENTS

WO    WO2007/133637 A2    11/2007

OTHER PUBLICATIONS

Burton, George et al., "Palladium-Catalyzed Intermolecular Coupling of Aryl Chlorides and Sulfonamides under Microwave Irradiation," Organic Letters (2003), vol. 5, No. 23, pp. 4373-4376.
Alcaraz, Lilian et al., "Novel N-Aryl and N-Heteroaryl Sulfamide Synthesis via Palladium Cross Coupling," Organic Letters (2004), vol. 6, No. 16, pp. 2705-2708.
Anjanappa, Prakash et al., "2-(Trimethylsilyl)ethanesulfonyl amide as a new ammonia equivalent for palladium-catalyzed amination of aryl halides," Tetrahedron Letters (2008), vol. 49, pp. 4585-4587.
Ikawa, Takashi et al., "Pd-Catalyzed Amidations of Aryl Chlorides Using Monodentate Biaryl Phosphine Ligands: A Kinetic, Computational, and Synthetic Investigation," Journal of the American Chemical Society (2007), vol. 129, pp. 13001-13007.
Yin, Jingjun et al., "Palladium-Catalyzed Intermolecular Coupling of Aryl Halides and Amides," Organic Letters (2000), vol. 2, No. 8, pp. 1101-1104.
Yin, Jingjun et al., "Pd-Catalyzed Intermolecular Amidation of Aryl Halides: The Discovery that Xantphos Can Be Trans-Chelating in a Palladium Complex," Journal of the American Chemical Society (2002), vol. 124, pp. 6043-6048.
International Search Report dated Jun. 28, 2011 issued in PCT/FR2011/050706.

*Primary Examiner* — Noble Jarrell
*Assistant Examiner* — Raymond Covington
(74) *Attorney, Agent, or Firm* — Scully, Scott, Murphy & Presser, P.C.

(57) ABSTRACT

The invention relates to a method for preparing 3-keto-benzofurane derivatives of the general formula: Formula (I), where R is an alkyl or aryl group, $R_1$ is hydrogen or an alkyl or aryl group, and $R_2$ is a substituted alkyl or phenyl group. Said preparation method involves coupling a derivative of Formula III, where X is chlorine, bromine, or iodine or a sulfonate grouping: Formula (III) with a sulfonamide derivative of the formula R—$SO_2$—$NH_2$ in the presence of a basic agent and a catalytic system formed of a complex between a palladium compound and a ligand.

15 Claims, No Drawings

METHOD FOR PREPARING 3-KETO-BENZOFURANE DERIVATIVES

The present invention relates, in general, to the preparation of 3-keto-benzofuran derivatives.

More specifically, the invention relates to a method for preparing 3-keto-benzofuran derivatives of general formula:

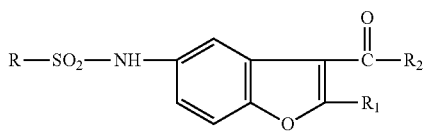

in which R represents an alkyl or aryl group, $R_1$ represents hydrogen or an alkyl or aryl group and $R_2$ represents an alkyl or phenyl group of general formula:

in which Y represents hydrogen, a halogen or a hydroxyl, alkoxy or dialkylaminoalkoxy group.

In formula I above:

R or $R_1$ represents, in particular, a linear or branched $C_1$-$C_8$ alkyl group, in particular a linear or branched $C_1$-$C_4$ alkyl group, such as methyl, ethyl, n-propyl, isopropyl, n-butyl, sec-butyl or tert-butyl or else a phenyl group that is substituted or unsubstituted, $R_2$ represents, in particular, a linear or branched $C_1$-$C_8$ alkyl group, in particular a linear or branched $C_1$-$C_4$ alkyl group such as methyl, ethyl, n-propyl, isopropyl, n-butyl, sec-butyl or tert-butyl or else a phenyl group of formula II in which Y represents, in particular, fluorine, chlorine, bromine or iodine or a linear or branched $C_1$-$C_8$ alkoxy group, in particular a linear or branched $C_1$-$C_4$ alkoxy group such as methoxy, ethoxy, n-propoxy, isopropoxy, n-butoxy, sec-butoxy or tert-butoxy or a dialkylaminoalkoxy group in which each linear or branched alkyl group is a $C_1$-$C_8$ and the linear or branched alkoxy group is a $C_1$-$C_8$, in particular in which each linear or branched alkyl group is a $C_1$-$C_4$ such as methyl, ethyl, n-propyl, isopropyl, n-butyl, sec-butyl or tert-butyl and the linear or branched alkoxy group is a $C_1$-$C_4$ such as methoxy, ethoxy, n-propoxy, isopropoxy, n-butoxy, sec-butoxy or tert-butoxy.

Among the group R, methyl may be mentioned, among the group $R_1$, n-butyl may be mentioned and among the group $R_2$, 4-[3-(di-n-butylamino)-propoxy]-phenyl may be mentioned.

The compounds of formula I above are, for the most part, compounds which are the subject of patent EP0471609 in which their preparation and their therapeutic applications, in particular in the cardiovascular field, are described. By way of example, 2-n-butyl-3-{4-[3-(di-n-butylamino)-propoxy]-benzoyl}-5-methanesulfonamido-benzofuran, commonly called dronedarone, and its pharmaceutically acceptable salts, has proved to be particularly advantageous, for example, as an antiarrhythmic agent.

Patent application WO0248132 describes a method for the synthesis of dronedarone using 2-n-butyl-5-nitro-benzofuran which is reduced, under pressure, with hydrogen in the presence of platinum oxide as catalyst in order to form 2-n-butyl-5-amino-benzofuran. This benzofuran derivative is then subjected to the action of methanesulfonyl chloride, which gives 2-n-butyl-5-methanesulfonamido-benzofuran which is treated with 4-[3-(di-n-butylamino)-propoxy]-benzoyl chloride to give dronedarone.

However, this method is not without disadvantages inherent in particular in the type of reaction used and in the reagents used, namely hydrogenation under pressure which comprises an industrial risk as well as a treatment with methanesulfonyl chloride, a dangerous reagent which can generate genotoxic impurities (methanesulfonates).

The search for a method for preparing dronedarone capable of overcoming these drawbacks and disadvantages therefore remains of paramount importance.

It has now been found that it is possible to obtain this compound, with good yield, using reagents and reaction steps that do not have the disadvantages and drawbacks previously reported because they do not involve either a catalytic hydrogenation reaction under pressure or the use of methanesulfonyl chloride.

According to the invention, the 3-keto-benzofuran derivatives of formula I may be prepared by coupling a benzofuran derivative of general formula:

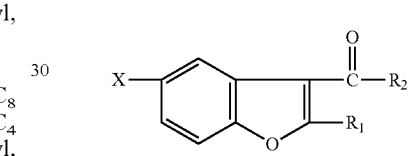

in which $R_1$ and $R_2$ have the same meanings as above and X represents chlorine, bromine or iodine or a sulfonate group of general formula:

in which $R_3$ represents a trifluoromethane (—$CF_3$) or imidazolyl group, with a sulfonamide derivative of general formula:

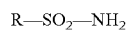

in which R has the same meaning as above, this being in the presence of a basic agent and a catalytic system formed of a complex between a palladium compound and a ligand, which gives the desired compounds.

The palladium complex used in the method of the invention is generally in the form of a palladium(0) compound such as for example:

tris(dibenzylideneacetone)dipalladium(0), called hereinafter "$Pd_2(dba)_3$" or, preferably, bis(dibenzylideneacetone)palladium(0), called hereinafter "$Pd(dba)_2$", and a ligand generally chosen from phosphines, usually biarylphosphines.

These biarylphosphines are generally substituted in various ways. Thus, the aryl, such as phenyl, ring not bearing the phosphorus atom may be mono- or, in particular, polysubstituted, for example, with the isopropyl group while the aryl, in particular phenyl, ring bearing the phosphorus atom may be moreover mono- or polysubstituted. In particular, this aryl ring does not comprise other substituents than the phosphorus atom.

The phosphorus atom, for its part, may itself be substituted, for example mono- or, preferably, disubstituted, for example with alkyl or cycloalkyl groups such as tert-butyl or cyclohexyl.

By way of example, the following compounds may be used as ligands:

2-(di-tert-butylphosphino)-2',4',6'-triisopropyl-1,1'-biphenyl, called hereinafter "ligand L1",
2-(di-cyclohexylphosphino)-2',4',6'-triisopropyl-1,1'-biphenyl, called hereinafter "ligand L2",
2-(di-cyclohexylphosphino)-2',6'-dimethoxy-1,1'-biphenyl, called hereinafter "ligand L3", 2-(di-tert-butylphosphino)-3,4,5,6-tetramethyl-2',4',6'-triisopropyl-1,1'-biphenyl, called hereinafter "ligand L4".

Ligand L1 is particularly advantageous.

The basic agent used in the method according to the invention may be chosen in particular from alcoholates, but more generally from weaker bases such as phosphates or carbonates, for example alkali metal phosphates or alkali metal carbonates such as tripotassium phosphate, potassium carbonate or cesium carbonate.

In general, the coupling reaction is carried out in the hot state, for example at a temperature between 60° C. and 120° C., and in an appropriate solvent. This may correspond to an alcohol such as tert-butanol, to an ether such as for example tetrahydrofuran or dioxane or to a hydrocarbon, in particular an aromatic hydrocarbon, such as for example toluene. Dioxane however constitutes a solvent of choice in the context of the present invention.

The starting compounds of formula III may be obtained as described below.

A.—The compounds of formula III in which X represents a chlorine, bromine or iodine atom (designated $X_1$ below) may be obtained by the reaction of a benzofuran derivative of general formula:

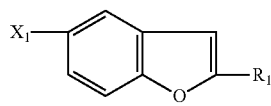

VI in which $R_1$ has the same meaning as above and $X_1$ represents a chlorine, bromine or iodine atom, with an acyl chloride of general formula:

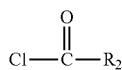

VII in which $R_2$ has the same meaning as above, in the presence of a Lewis acid as catalyst, for example aluminum chloride.

The compounds of formula VI described above may be obtained according to the following reaction scheme:

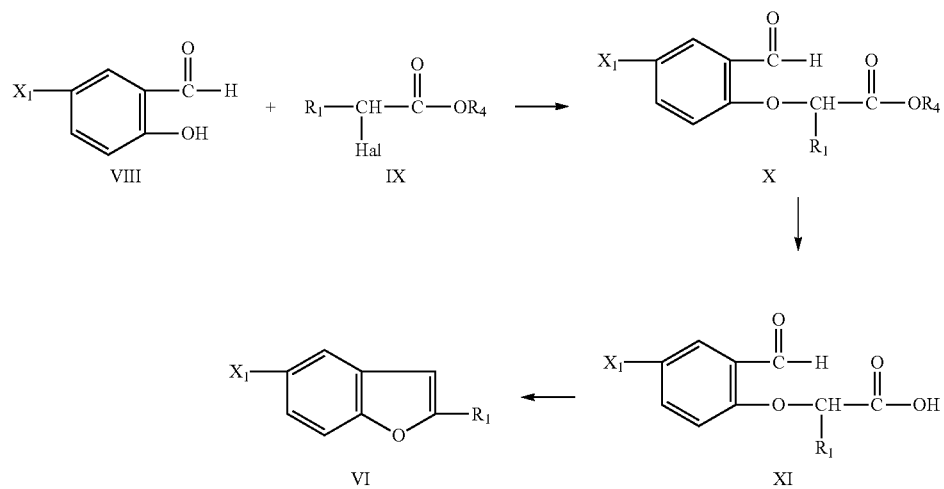

that is to say starting with a 2-hydroxy-phenyl derivative of formula VIII in which $X_1$ represents chlorine, bromine or iodine, which is reacted with a haloester of formula IX in which $R_1$ has the same meaning as above, Hal represents a halogen, in particular bromine, and $R_4$ represents a $C_1$-$C_4$ alkyl group, such as for example ethyl, to form an ester of formula X in which $R_1$, $R_4$ and $X_1$ have the same meanings as above.

The reaction is generally carried out by heating in an appropriate solvent, in particular a polar solvent such as N,N-dimethylformamide, and in the presence of a basic agent such as an alkali metal carbonate.

The ester of formula X is then saponified in a solvent, in particular an ether, and in the presence of an appropriate basic agent such as an alkali metal hydroxide to form the corresponding metal salt of a carboxylic acid derivative which is then treated with a strong acid in a solvent such as an aromatic hydrocarbon, to give the carboxylic acid derivative of formula XI in which $R_1$ and $X_1$ have the same meanings as above.

In a subsequent step, the carboxylic acid derivative of formula XI is then cyclized by heating in the presence of a benzenesulfonyl halide, for example chloride, and of an acid acceptor such as a tertiary amine, the reaction generally taking place by heating in a solvent such as an aromatic hydrocarbon, to give the desired compounds of formula VI.

B.—The compounds of formula III in which X represents a sulfonate group of formula IV may be obtained according to the following reaction scheme:

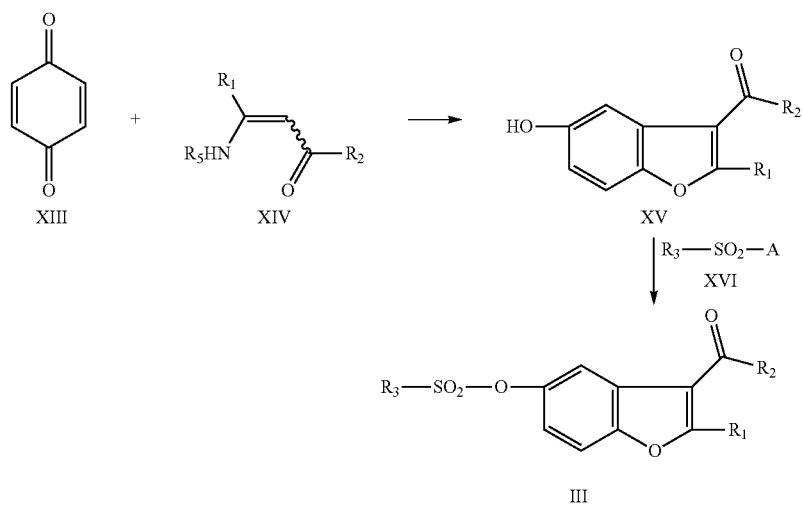

namely a 1,4-benzoquinone of formula XIII is treated with an enamine of formula XIV in which $R_1$ and $R_2$ have the same meanings as above, and in which $R_5$ represents a hydrogen atom, a linear or branched $C_1$-$C_4$ alkyl group, or a phenyl group optionally substituted at the para position with a $C_1$-$C_4$ alkyl or $C_1$-$C_4$ alkoxy group.

Alternatively, the reagent of formula XIV may be a dimer, that is to say that the substituent $R_5$ represents an alkylene bridge between two identical monomers, in which case the reagent XIV corresponds to the following formula XIV-bis:

in which:

Y represents a group of the following formula, in which $R_1$ and $R_2$ are as defined above (cf. formula XIV):

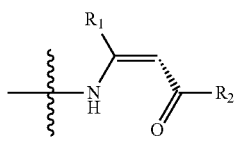

L represents an alkylene bridge, for example a $C_1$-$C_{10}$.

The reaction between the compounds of formulae XIII and XIV or XIV-bis is carried out in an acidic solvent, for example acetic acid. It leads to the 5-hydroxy-benzofuran derivatives of formula XV in which $R_1$ and $R_2$ have the same meanings as above.

The compound of formula XV is then coupled with a sulfonyl derivative of formula XVI in which Hal has the same meaning as above, in particular chlorine, and $R_3$ has the same meaning as above, this being in the presence of an acid acceptor, in particular pyridine, which gives the sulfonate derivatives of formula III in which $R_1$, $R_2$ and $R_3$ have the same meanings as above.

The substituent A may represent Hal or $-OSO_2R_3$. In particular, when $R_3$ represents a trifluoromethane, then A represents $-OSO_2CF_3$.

The benzofuran derivatives of general formula:

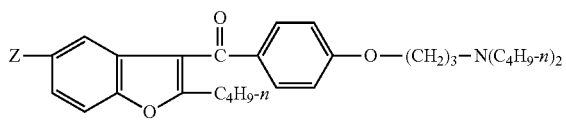

in which Z represents a halogen, for example bromine, the hydroxyl group or a sulfonate group of formula $-O-SO_2R_3$ in which $R_3$ represents a trifluoromethane or imidazolyl group, represent another subject of the present invention.

The following nonlimiting examples illustrate the invention. In these examples, the abbreviations below are used:
TLC: thin-layer chromatography
HPLC: high-performance liquid chromatography
NMR: nuclear magnetic resonance

PREPARATIONS

I. 2-n-Butyl-5-bromo-benzofuran (compound VI: $R_1$=n-$C_4H_9$; X=Br)

A. Ethyl 2-(4-bromo-2-formylphenoxy)-hexanoate (compound X: $R_1$=n-$C_4H_9$; $R_4$=$C_2H_5$; $X_1$=Br)

8.9 g of potassium carbonate (64.3 mmol) and 45 ml of N,N-dimethylformamide are placed in an equipped reactor and then heated to 55° C. with stirring. A solution of 22 g of 2-hydroxy-5-bromo-benzeneformaldehyde (compound VIII: $X_1$=Br) (107.2 mmol) in 40 ml of N,N-dimethylformamide is then poured dropwise over the mixture at 55° C.; the dropping funnel is rinsed with 10 ml of N,N-dimethylformamide. The medium is stirred at 55° C. for 30 minutes and then heated to 80° C. 20.8 ml of ethyl 2-bromohexanoate (compound IX: $R_1$=n-$C_4H_9$; $R_4$=$C_2H_5$; Hal=Br) (112.6 mmol) are added, and the dropping funnel is rinsed with 10 ml of N,N-dimethylformamide. The reaction medium is kept at 80° C. with stirring: the progress of the reaction is monitored by TLC (eluent: methylcyclohexane/ethyl acetate: 7/1; Rf of compound VIII: 0.53; Rf of compound X: 0.44).

At the end of the reaction, the temperature of the reaction medium is brought to 20° C. and then 100 ml of deionized water are slowly added, leading to the demixing of an oil. This oil is decanted off and separated from the aqueous phase and then washed with 100 ml of water. After decantation and separation, the oil is diluted with 60 ml of toluene and then this organic phase is again washed with 100 ml of deionized water. The latter aqueous phase is back-extracted with 60 ml of ethyl acetate. The organic phases are combined and then concentrated with a rotary evaporator to give 34.9 g of the desired compound X in the form of an orange yellow oil.

Yield: 95%

$^1$H NMR (400 MHz, CDCl$_3$): δ 0.93 (t, J=7.4 Hz, 3H, —CH$_2$—CH$_2$—CH$_3$); 1.23 (t, J=7 Hz, 3H, —O—CH$_2$—CH$_3$); 1.36-1.43 (m, 2H, —CH$_2$—CH$_2$—CH$_3$); 1.46-1.54 (m, 2H, —CH$_2$—CH$_2$—CH$_2$—); 1.99-2.05 (m, 2H, —CH$_2$—CH$_2$—CH—); 4.20 (q, J=7.2 Hz, 2H, —O—CH$_2$—CH$_3$); 4.71 (t, J=6 Hz, 1H, —CH$_2$—CH—O—); 6.71 (d, J=8.8 Hz, 1H, ArH); 7.56 (dd, J=9 and 2.6 Hz, 1H, ArH); 7.94 (d, J=2.4 Hz, 1H, ArH); 10.49 (s, 1H, CHO)

$^{13}$C NMR (CDCl$_3$): δ 188.3-170.6-159.3-138.1-131.1-126.9-115.2-114.5-77.4-61.6-32.3-27.3-22.3-14.2-13.9 ppm B. 2-(4-Bromo-2-formylphenoxy)-hexanoic acid (compound XI: R$_1$=n-C$_4$H$_9$; X$_1$=Br)

60 g of ethyl 2-(4-bromo-2-formylphenoxy)-hexanoate (compound X) (0.17 mmol) and 52 ml of methyl tert-butyl ether are placed in an equipped reactor. 78 ml of deionized water and a solution of 9.37 g of 23% sodium hydroxide (0.23 mmol) in 31.4 g of deionized water are added at 20° C. The reaction medium is heated to 40° C. with stirring and the saponification of the ester is monitored by TLC (eluent: methylcyclohexane/ethyl acetate 8/2+ a few drops of acetic acid; Rf of compound X=0.52; Rf of compound XI: 0.08).

At the end of the reaction, the temperature of the reaction medium is brought to 20° C. and 25.5 g of sodium chloride (0.43 mol) in 130 ml of deionized water and then 270 ml of toluene are added. The reaction medium is acidified by the slow addition of 20 ml of a 37% hydrochloric acid solution, without exceeding 25° C., with stirring. The two phases are decanted off and separated, and then the organic phase is washed with 80 ml of deionized water. After separation of the phases, the organic phase is concentrated under vacuum with a rotary evaporator to give 54.7 g of a red oil which crystallizes in the cold state.

After slurrying again in a diisopropyl ether/heptane mixture, 45.5 g of the desired compound XI are isolated in the form of a yellow-white solid.

Yield: 82%

$^1$H NMR (400 MHz, CDCl$_3$): δ 0.93 (t, J=7.2 Hz, 3H, —CH$_2$—CH$_2$—CH$_3$); 1.37-1.44 (m, 2H, —CH$_2$—CH$_2$—CH$_3$); 1.49-1.57 (m, 2H, —CH$_2$—CH$_2$—CH$_2$—); 2.05-2.11 (m, 2H, —CH$_2$—CH$_2$—CH—); 4.79 (t, J=6 Hz, 1H, —CH$_2$—CH—CO—); 6.78 (d, J=8.8 Hz, 1H, ArH); 7.61 (dd, J=8.8 and 2.4 Hz, 1H, ArH); 7.94 (d, J=2.4 Hz, 1H, ArH); 10.39 (s, 1H, CHO)

$^{13}$C NMR (CDCl$_3$): δ 188.6-174.3-158.6-138.3-132.4-127.0-115.5-114.9-77.2-32.2-27.1-22.3-13.8 ppm C. 2-n-Butyl-5-bromo-benzofuran (compound XII: R$_1$=n-C$_4$H$_9$; X$_1$=Br)

25.8 ml of benzenesulfonyl chloride (0.202 mol; 1.4 equivalent) and 40 ml of toluene are placed in an equipped reactor and the mixture is stirred at 80° C. 65 ml of anhydrous triethylamine (0.47 mol) and then 45.2 g of 2-(4-bromo-2-formylphenoxy)-hexanoic acid (compound XI) (0.144 mol) in solution in 250 ml of toluene are slowly added at 80° C. The progress of the reaction is monitored by TLC (eluent: methylcyclohexane/ethyl acetate: 80/20; Rf of compound XI=0.08; Rf of the desired compound XII=0.80).

At the end of the reaction, the temperature of the reaction medium is brought to 20° C. The excess benzenesulfonyl chloride is destroyed by the addition of 250 ml of a 5% aqueous sodium hydroxide solution. The phases are decanted off and separated and then the organic phase is washed with a mixture of 70 ml of deionized water and 6.8 ml of 37% hydrochloric acid. The phases are decanted off and separated and then the organic phase is washed with 75 ml of deionized water. The organic phase is washed with a solution of 7.73 g of sodium hydroxide in solution in 67 ml of deionized water. The phases are decanted off and separated and then the organic phase is washed with a solution of 7.53 g of sodium chloride in 70 ml of deionized water. The pH of the aqueous phase is adjusted to between 5 and 8 with the aid of a 7% hydrochloric acid solution. The phases are decanted off and separated and then the organic phase is concentrated with a rotary evaporator to give 37.2 g of a brown oil.

This oil is purified by silica gel chromatography (eluent: methylcyclohexane/ethyl acetate: 80/20) to give 24.3 g of the desired compound XII in the form of a yellow oil.

Yield: 67%

$^1$H NMR (400 MHz, DMSO-d6): δ 0.91 (t, J=7.2 Hz, 3H, —CH$_2$—CH$_2$—CH$_3$); 1.30-1.40 (m, 2H, —CH$_2$—CH$_2$—CH$_3$); 1.61-1.69 (m, 2H, —CH$_2$—CH$_2$—CH$_2$—); 2.76 (t, J=7.4 Hz, 2H, —CH$_2$—CH$_2$-Cq); 6.57 (s, 1H, ArH); 7.33 (dd, J=8.8 and 2 Hz, 1H, ArH); 7.46 (d, J=8.8 Hz, 1H, ArH); 7.72 (dd, J=2 Hz, 1H, ArH)

II. 2-n-Butyl-3-{4-[3-(di-n-butylamino)-propoxy]-benzoyl}-5-bromo-benzofuran (compound III: X=Br; R$_1$=n-C$_4$H$_9$; R$_2$=4-[3-(di-n-butylamino)-propoxy]-phenyl)

A. 1-Chloro-3-(di-n-butylamino)-propane 18.6 g of 68.4% 1-chloro-3-(di-n-butylamino)-propane hydrochloride (52.6 mmol) are placed in an equipped reactor and then 9.97 g of a 20% aqueous ammonia solution (56.9 mmol) are added at 20° C. The mixture is stirred for 15 minutes, and then the phases are decanted off and separated: the bottom phase consists of 1-chloro-3-(di-n-butylamino)-propane in the form of a free base. This phase is washed with 10 ml of water and 9.99 g of 1-chloro-3-(di-n-butylamino)-propane are thus isolated.

B. Ethyl 4-[3-(di-n-butylamino)-propoxy]-benzoate (compound XIX: R$_2$=4-[3-(di-n-butylamino)-propoxy]-phenyl; R$_4$=C$_2$H$_5$)

7.3 g of potassium carbonate (52.6 mmol), 7 g of ethyl 4-hydroxy-benzoate (compound XXI: R$_4$=C$_2$H$_5$) (42.1 mmol) and 56 ml of N,N-dimethylformamide are placed in an equipped reactor. The reaction medium is heated to 95° C. and then the 1-chloro-3-(di-n-butylamino)-propane previously obtained is poured in dropwise. The reaction medium is stirred for 30 minutes at 95-100° C. and then cooled. The salts are filtered at 20° C. and then washed with twice 10 ml of N,N-dimethylformamide. The yellowish solution obtained is concentrated under vacuum with a rotary evaporator to give 15.6 g of the desired compound XIX in the form of a yellow oil.

$^1$H NMR (400 MHz, CDCl$_3$): δ 0.88 (t, J=7.2 Hz, 6H, 2*CH$_3$—CH$_2$—CH$_2$—); 1.23-1.33 (m, 4H, 2*CH$_3$—CH$_2$—CH$_2$—); 1.35-1.43 (m+t, 4H+3H, 2*CH$_3$—CH$_2$—C

H$_2$—CH$_2$—+CH$_3$—CH$_2$—O); 1.87-1.94 (m, 2H, —CH$_2$—CH$_2$—O—); 2.40 (t, J=7.4 Hz, 4H, 2*—CH$_2$—N); 2.57 (t, J=7 Hz, 2H, N—CH$_2$—); 4.06 (t, J=6.4 Hz, 2H, CH$_2$—CH$_2$—O); 4.33 (q, J=7.2 Hz, 2H, O—CH$_2$—CH$_3$); 6.89 (d, J=9.2 Hz, 2H, 2*ArH); 7.98 (d, J=8, 8 Hz, 2H, 2*ArH)

$^{13}$C NMR (CDCl$_3$): δ 162.9-131.5-122.7-114.0-101.0-66.5-60.6-54.0-50.4-29.4-27.1-20.7-14.4-14.1 ppm

C. 4-[3-(Di-n-butylamino)-propoxy]-benzoic acid hydrochloride (compound XX: R$_2$=4-[3-(di-n-butylamino)-propoxy]-phenyl)

35 ml of ethanol and 8.4 g of a 30% sodium hydroxide solution (63.2 mmol) are placed in an equipped reactor. The reaction medium is heated to 60° C. and then 15.6 g of ethyl 4-[3-(di-n-butylamino)-propoxy]-benzoate (compound XIX) previously obtained are poured in dropwise. The reaction medium is stirred for one hour under reflux and then the ethanol is evaporated under vacuum with a rotary evaporator. The acid in carboxylate form is dissolved in 45 ml of isopropanol and then 23 ml of 37% hydrochloric acid are added dropwise at 20° C.: the mixture is stirred for 1 hour at 15° C. The suspension is filtered and the solid is washed with 3 times 8 ml of water and then 10 ml of acetone. The solid is dried under vacuum at 60° C. to give 12.6 g of the desired compound XX in the form of white crystals.

Overall yield: 86.7%

$^1$H NMR (400 MHz, CDCl3): δ 0.92 (t, J=7.4 Hz, 6H, 2*CH$_3$—CH$_2$—CH$_2$—); 1.32-1.41 (m, 4H, 2*CH$_3$—CH$_2$—CH$_2$—); 1.63-1.71 (m, 4H, 2*CH$_3$—CH$_2$—CH$_2$—); 2.18-2.25 (m, 2H, —CH$_2$—CH$_2$—O—); 3.17 (t, J=8.2 Hz, 4H, 2*—CH$_2$—N); 3.36 (t, J=7.8 Hz, 2H, N—CH$_2$—); 4.23 (t, J=5.8 Hz, 2H, —CH$_2$—O); 7.06 (d, J=9.2 Hz, 2H, 2*ArH); 7.99 (d, J=9.2 Hz, 2H, 2*ArH)

$^{13}$C NMR (D$_2$O): δ 173.2-165.0-134.9-125.4-117.5-68.0-53.8-52.9-28.1-25.9-22.1-15.6 ppm

D. 4-[3-(Di-n-butylamino)-propoxy]-benzoic acid chloride hydrochloride (compound VII: R$_2$=4-[3-(di-n-butylamino)-propoxy]-phenyl)

10 g of 4-[3-(di-n-butylamino)-propoxy]-benzoic acid hydrochloride (compound XX) (29 mmol) and 31 ml of dichloromethane are placed in an equipped reactor. The mixture is heated under reflux and then 3.5 g of thionyl chloride (30 mmol) are slowly added (gaseous emission). The reaction medium is kept under reflux for at least 15 minutes after the end of the gaseous emission; the progress of the reaction is monitored by HPLC.

When the conversion of the acid is complete, the reaction medium is evaporated under vacuum to constant mass to give 10.3 g of the desired compound VII in the form of an orange-colored oil.

Crude yield: 98%

E. 2-n-Butyl-3-{4-[3-(di-n-butylamino)-propoxy]-benzoyl}-5-bromo-benzofuran hydrochloride (hydrochloride of compound III: X=Br; R$_1$=n-C$_4$—H$_9$; R$_2$=4-[3-(di-n-butylamino)-propoxy]-phenyl)

5 g of 2-n-butyl-5-bromo-benzofuran (compound VI) (19.7 mmol), 35 ml of dichloromethane and 7.23 g of 4-[3-(di-n-butylamino)-propoxy]-benzoic acid chloride hydrochloride (compound VII) (19.7 mmol) are placed in an equipped reactor under an inert atmosphere. 1.4 g of aluminum chloride are added all at once at room temperature, with vigorous stirring. The reaction medium is kept stirring for 10 minutes and then 9.2 g of aluminum chloride are again added while keeping the temperature of the mass below 30° C. The reaction medium is kept stirring for 2 to 3 hours according to the progress of the reaction. At the end of the reaction, the medium is cooled to 15° C. for hydrolysis.

30 ml of water are placed in a second reactor and cooled to 5° C. The reaction medium is poured over water while keeping the temperature below 30° C. The first reactor is rinsed with 5 ml of dichloromethane. After the end of the pouring, the hydrolysis medium is stirred for 30 minutes at 20° C. The phases are decanted off and separated and then the organic phase is concentrated under vacuum with a rotary evaporator.

The crude product is then purified by silica gel chromatography (eluent: ethyl acetate/methylcyclohexane and then ethanol) to give 7.75 g of the desired compound III in the form of a dark yellow oil.

Yield: 67%

$^1$H NMR (400 MHz, CDCl3): δ 0.79 (t, J=7.4 Hz, 3H, CH$_3$—CH$_2$—CH$_2$—); 0.91 (t, J=7.6 Hz, 6H, 2*CH$_3$—CH$_2$—CH$_2$—); 1.18-1.27 (m, 2H, CH$_3$—CH$_2$—CH$_2$—); 1.28-1.37 (m, 4H, 2*CH$_3$—CH$_2$—CH$_2$—); 1.61-1.71 (m, 6H, 2*—CH$_3$—CH$_2$—CH$_2$—CH$_2$—+CH$_3$—CH$_2$—CH$_2$—CH$_2$—); 2.18-2.25 (m, 2H, —CH$_2$—CH$_2$—O—); 2.80 (t, J=7.4 Hz, 2H, CH$_2$—CH$_2$—CH$_2$—CH$_3$); 3.05 (t, J=8.2 Hz, 4H, 2*—CH$_2$—N); 3.22 (t, J=7.8 Hz, 2H, N—CH$_2$—); 4.20 (t, J=5.6 Hz, 2H, —CH$_2$—O); 7.10 (d, J=8.4 Hz, 2H, 2*ArH); 7.49 (d, J=6.4 Hz, 2H, 2*ArH); 7.64 (d, J=9.2 Hz, 1H, 2*ArH); 7.78 (d, J=8.4 Hz, 2H, 2*ArH)

$^{13}$C NMR (DMSO-d6): δ 188.8-164.9-162.2-151.9-131.3-131.0-128.8-127.2-122.9-115.9-115.7-114.4-113.2-65.2-51.6-48.7-29.2-27.1-24.8-22.8-21.5-19.4-13.4-13.3 ppm

F. 2-n-Butyl-3-{4-[3-(di-n-butylamino)-propoxy]-benzoyl}-5-bromo-benzofuran (compound III: X=Br; R$_1$=n-C$_4$—H$_9$; R$_2$=4-[3-(di-n-butylamino)-propoxy]-phenyl)

6 ml of a 20% aqueous potassium carbonate solution are added to a solution of 1.3 g of 2-n-butyl-3-{4-[3-(di-n-butylamino)-propoxy]-benzoyl}-5-bromo-benzofuran hydrochloride (hydrochloride of compound III) in 20 ml of dichloromethane in a round-bottomed flask. The phases are decanted off and separated and then the aqueous phase is back-extracted with twice 20 ml of dichloromethane. The organic phases are combined and concentrated with a rotary evaporator to give 1 g of the desired compound III in the form of a yellow oil.

Yield: 82%

III. 2-Butyl-3-({4-[3-(dibutylamino)propoxy]phenyl}carbonyl)-1-benzofur-5-yl trifluoromethanesulfonate

A. (2-Butyl-5-hydroxy-1-benzofur-3-yl){4-[3-(dibutylamino)propoxyl]phenyl}methanone hydrochloride (compound XV: R$_1$=n-C$_4$H$_9$; R$_2$=4-[3-(di-n-butylamino)-propoxy]-phenyl)

20 g of (2E,2'E)-3,3'-(1,4-butanediyldiimino)bis(1-{4-[3-(dibutylamino)propoxy]phenyl}-2-hepten-1-one) (24.06 mmol) and 40 ml of acetic acid are placed in an equipped reactor. The reaction medium is stirred and then a solution of 5.2 g of benzo-1,4-quinone (48.12 mmol) in 40 ml of acetic acid is slowly added. The reaction medium is stirred at room temperature for 30 minutes. The progress of the reaction is monitored by TLC. The reaction medium is concentrated with a rotary evaporator and then taken up in dichloromethane, and then washed with an aqueous potassium hydroxide solution. The phases are decanted off and separated, and then the organic phase is acidified by the addition of hydrochloric acid and then concentrated with a rotary evaporator. The crude product is then purified by silica gel chromatography.

The evaporation of the pure fractions leads to the isolation of 19.3 g of product in the form of a yellow oil.

Yield: 77%.

$^1$H NMR (500 MHz, CDCl$_3$): δ 0.90 (t, J=7.5 Hz, 3H, CH$_3$—CH$_2$—CH$_2$—); 0.93 (t, J=7.5 Hz, 6H, 2*CH$_3$—CH$_2$—CH$_2$—); 1.28-1.42 (m, 6H, 3*CH$_3$—CH$_2$—CH$_2$—CH$_2$—); 1.60 (m, 4H, 2*CH$_3$—CH$_2$—CH$_2$—CH$_2$—); 1.75 (q, J=7.5 Hz, 2H, CH$_3$—CH$_2$—CH$_2$—CH$_2$—); 2.19 (m, 2H, —CH$_2$—CH$_2$—O—); 2.90 (m, 4H, 2*CH$_3$—CH$_2$—CH$_2$—CH$_2$—N); 2.95 (t, J=7.5 Hz, 2H, CH$_3$—CH$_2$—CH$_2$—CH$_2$); 3.08 (t, J=7.5 Hz, 2H, CH$_2$—N—); 4.16 (t, J=5.5 Hz, 2H, O—CH$_2$—); 6.61 (d, J=2.5 Hz, 1H, system type 1,2,4); 6.80 (dd, J=9.0, J=2.5 Hz, 1H, system type 1,2,4); 6.89 (d, J=9.0 Hz, 2*1H, system type 1,4); 7.27 (d, J=9.0 Hz, 1H, system type 1,2,4); 7.75 (d, J=9.0 Hz, 2*1H, system type 1,4).

$^{13}$C NMR (500 MHz, CDCl$_3$): δ 191.0-166.3-161.6-153.7-148.1-132.6-131.4-127.7-116.7-114.5-113.2-111.3-106.3-65.0-51.5-49.9-30.2-28.0-25.3-24.0-22.4-20.3-13.8-13.7 ppm.

B. 2-Butyl-3-({4-[3-(dibutylamino)propoxy]phenyl}carbonyl)-1-benzofur-5-yl trifluoromethanesulfonate (compound XVIII: Z: —OSO$_2$R$_3$ and R$_3$: trifluoromethane)

4 g of 2-n-butyl-3-{4-[3-(di-n-butylamino)-propoxy]-benzoyl}-5-hydroxy-benzofuran hydrochloride (8 mmol) and 16 ml of dichloromethane are placed in an equipped reactor. The reaction medium is stirred until dissolution is obtained. An aqueous sodium bicarbonate solution is added to the reaction medium to pH>7.5 and then the medium is stirred. The phases are decanted off and separated. The aqueous phase is extracted with dichloromethane and then the combined organic phases are washed with a saline solution. After concentration of the organic phase, 3.38 g of 2-n-butyl-3-{4-[3-(di-n-butylamino)-propoxy]-benzoyl}-5-hydroxy-benzofuran are isolated in the form of a brown oil.

3 g of 2-n-butyl-3-{4-[3-(di-n-butylamino)-propoxy]-benzoyl}-5-hydroxy-benzofuran (6.25 mmol) and 12 ml of dichloromethane are placed in a 25 ml equipped reactor. The reaction medium is stirred until complete dissolution is obtained. Next, 0.5 ml of pyridine (6.25 mmol) is added. After stirring for 5 minutes, 1.05 ml of triflic anhydride (6.25 mmol) are added to the reaction medium which is stirred for an additional 5 minutes. The end of the reaction is monitored by TLC.

When the reaction is complete, 12 ml of 0.1 N hydrochloric acid are added to the reaction medium. The phases are decanted off and separated. The organic phase is successively washed with an aqueous sodium bicarbonate solution and then with water. The organic phase is concentrated with a rotary evaporator to give 4.39 g of crude product in the form of a brown oil.

3 g of crude product are then purified by silica gel chromatography. Evaporation of the pure fractions leads to the isolation of 2.22 g of expected product in the form of a yellow oil.

Yield: 76%.

$^1$H NMR (500 MHz, CDCl$_3$): δ 0.89 (t, J=7.5 Hz, 3H, CH$_3$—CH$_2$—CH$_2$—); 0.93 (t, J=7.5 Hz, 6H, 2*CH$_3$—CH$_2$—CH$_2$—); 1.35 (sext, J=7.5 Hz, 6H, 3*CH$_3$—CH$_2$—CH$_2$—); 1.55 (broad signal, 4H, 2*CH$_3$—CH$_2$—CH$_2$—); 1.75 (q, J=7.5 Hz, 2H, CH$_3$—CH$_2$—CH$_2$—); 2.10 (broad signal, 2H, —CH$_2$—CH$_2$—O—); 2.68 (broad signal, 4H, 2*CH$_3$—CH$_2$—CH$_2$—CH$_2$—N); 2.87 (broad signal, 2H, CH$_2$—N—); 2.92 (t, J=7.5 Hz, 2H, CH$_3$—CH$_2$—CH$_2$—CH$_2$—); 4.14 (t, J=6.0 Hz 2H, O—CH$_2$—); 6.96 (d, J=9.0 Hz, 2*1H, system type 1,4); 7.18 (dd, J=9.0, J=2.5 Hz, 1H, system type 1,2,4); 7.30 (d, J=2.5 Hz, 1H, system type 1,2,4); 7.51 (d, J=9.0 Hz, 1H, system type 1,2,4); 7.81 (d, J=9.0 Hz, 2*1H, system type 1,4)

$^{13}$C NMR (500 MHz, CDCl$_3$): δ 189.4-167.2-163.0-152.2-145.7-131.7-131.3-128.6-118.8 (quad, J$_{CF}$=321 Hz)-117.5-117.0-114.4-112.2-66.0-53.7-50.7-30.0-28.0-27.8*-26.0*-22.4-20.5-13.9-13.7

*recorded on the HMQC map.

EXAMPLES

Example 1

2-n-Butyl-3-{4-[3-(di-n-butylamino)-propoxy]-benzoyl}-5-methanesulfonamido-benzofuran or dronedarone (compound I: R=CH$_3$; R$_1$=n-C$_4$H$_9$; R$_2$=4-[3-(di-n-butylamino)-propoxy)-phenyl)

360 mg of cesium carbonate (1.11 mmol) and 79 mg of methanesulfonamide (0.83 mmol), 9.5 mg of Pd(dba)$_2$ (0.01 mmol) and 14.5 g of 2-(di-tert-butylphosphino)-2',4',6'-tri-isopropyl-1,1'-biphenyl (ligand L1) (0.03 mmol) are introduced into a 20 ml tube previously dried in an oven. The tube is sealed with a septum and inerted with argon and then 300 mg of 2-n-butyl-3-{4-[3-(di-n-butylamino)-propoxy]-benzoyl}-5-bromo-benzofuran (compound III) (0.55 mmol) in solution in 2 ml of dioxane are added with a syringe. The reaction medium is then stirred and heated under the reflux temperature of dioxane for 24 hours, while monitoring the progress of the reaction by HPLC.

At the end of the reaction, the desired compound I is obtained.

Yield: 78%

$^1$H NMR (400 MHz, CDCl$_3$): δ 0.81 (t, J=7.4 Hz, 3H, CH$_3$—CH$_2$—CH$_2$—); 0.91 (t, J=7.4 Hz, 6H, 2*CH$_3$—CH$_2$—CH$_2$—); 1.18-1.28 (m, 2H, CH$_3$—CH$_2$—CH$_2$—); 1.28-1.38 (m, 4H, 2*CH$_3$—CH$_2$—CH$_2$—); 1.62-1.70 (m, 6H, 2*CH$_3$—CH$_2$—CH$_2$—CH$_2$—+CH$_3$—CH$_2$—CH$_2$—CH$_2$—); 2.18-2.22 (m, 2H, —CH$_2$—CH$_2$—O—); 2.80 (t, J=7.4 Hz, 2H, —CH$_2$—CH$_2$—CH$_2$—CH$_3$); 2.88 (s, 3H, CH$_3$—S—); 3.03-3.08 (m, 4H, 2*CH$_2$—CH$_2$—NH$^+$); 3.19-3.24 (m, 2H, NH$^+$—CH$_2$—); 4.19 (t, J=6 Hz, 2H, —CH$_2$—O); 7.09 (d, J=8.8 Hz, 2H, 2*ArH); 7.21 (dd, J=8.8 Hz and 2.4 Hz, 1H, 2*ArH); 7.28 (d, J=2.4 Hz, 1H, 2*ArH); 7.62 (d, J=8.8 Hz, 1H, 2*ArH); 7.79 (d, J=8.8 Hz, 2H, 2*ArH)

$^{13}$C NMR (DMSO-d6): δ 189.1-164.4-162.6-150.2-134.2-131.3-130.7-127.2-118.7-116.3-114.3-113.1-111.5-65.9-53.2-49.5-38.5-29.3-28.8-27.1-26.4-21.5-19.9-13.3 ppm Example 2

2-n-Butyl-3-{4-[3-(d i-n-butylamino)-propoxy]-benzoyl}-5-methanesulfonamido-benzofuran or dronedarone (compound I: R=CH$_3$; R$_1$=n-C$_4$H$_9$; R$_2$=4-[3-(di-n-butylamino)-propoxy)-phenyl)

1.73 g of cesium carbonate (5.33 mmol), 0.38 g of methanesulfonamide (4 mmol), 46 mg of the catalyst Pd(dba)$_2$ (0.08 mmol) and 67.9 mg of ligand di-tert-butyl(2',4',6'-triisopropylbiphenyl-2-yl)phosphine (0.16 mmol) are introduced into a 20 ml tube previously dried in an oven. Next, 1.63 g of 2-butyl-3-({4-[3-(dibutylamino)propoxy]phenyl}carbonyl)-1-benzofur-5-yl trifluoromethanesulfonate in solution in 11.4 ml of dioxane are added to the reaction medium. The reaction medium is then stirred and heated at the reflux temperature of dioxane for 24 hours, while monitoring the progress of the reaction by TLC. The medium is filtered. An MTBE/THF mixture is added and then water in order to remove the salts. The reaction medium is concentrated by concentrating with the MTBE/THF mixture in order to remove the dioxane. 1.63 g of crude product are thus obtained in the form of a brown oil.

The crude product is then taken up in isopropyl alcohol (iPA) and then concentrated by distillation of the iPA: the volume is adjusted to 6.52 ml and the reaction medium is heated to 50° C. 0.29 ml of 37% hydrochloric acid (3 mmol) is poured dropwise into the reaction medium while keeping the temperature at 50-55° C. After rinsing with 0.35 ml of iPA, the reaction medium is stirred at 50° C. for 10 minutes. The medium is then heated at 65° C. in order to obtain complete solubilization and then cooled to 51° C. 28.5 mg of initiator are then added. The medium is then stirred for 40 minutes at 51° C. and then cooled to 41° C. over 45 minutes, stirred for 30 minutes at 41° C., heated again to 51° C. over 10 minutes, stirred for 30 minutes at 51° C. and finally cooled to 10° C. over 4 h 45 min. After filtration of the reaction medium and several rinses with iPA, the product is dried. 0.89 g of dronedarone is obtained in the form of a cream-colored powder.

Yield: 56%.

The invention claimed is:

1. A method for preparing 3-keto-benzofuran derivatives of general formula:

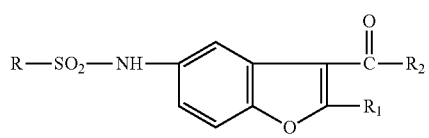

I in which R represents an alkyl or aryl group, $R_1$ represents hydrogen or an alkyl or aryl group and $R_2$ represents an alkyl or phenyl group of general formula:

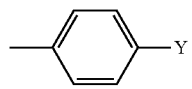

II in which Y represents hydrogen, a halogen or a hydroxyl, alkoxy or dialkylaminoalkoxy group, where a benzofuran derivative of general formula:

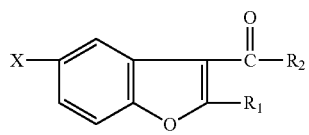

III in which $R_1$ and $R_2$ have the same meanings as above and X represents chlorine, bromine or iodine or a sulfonate group of general formula:

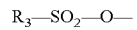

IV in which $R_3$ represents a trifluoromethane or imidazolyl group; is coupled with a sulfonamide derivative of general formula:

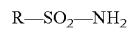

V in which R has the same meaning as above, in the presence of a basic agent and a catalytic system formed of a complex between a palladium compound and a ligand.

2. The method as claimed in claim 1, wherein:
R or $R_1$ represents a linear or branched $C_1$-$C_8$ alkyl group or a phenyl group that is substituted or unsubstituted,
$R_2$ represents a linear or branched $C_1$-$C_8$ alkyl group or a phenyl group of formula II in which Y represents chlorine, bromine or iodine or a linear or branched $C_1$-$C_8$ alkoxy group or a dialkylaminoalkoxy group in which each linear or branched alkyl group is a $C_1$-$C_8$ and the linear or branched alkoxy group is a $C_1$-$C_8$.

3. The method as claimed in claim 2, wherein:
R or $R_1$ represents a linear or branched $C_1$-$C_4$ alkyl group,
$R_2$ represents a linear or branched $C_1$-$C_4$ alkyl group or a phenyl group of formula II in which Y represents a $C_1$-$C_4$ alkoxy group or a dialkylaminoalkoxy group in which each linear or branched alkyl group is a $C_1$-$C_4$ and the linear or branched alkoxy group is a $C_1$-$C_4$.

4. The method as claimed in claim 1, wherein R represents methyl, $R_1$ represents n-butyl and $R_2$ represents 4-[3-(di-n-butylamino)-propoxy]-phenyl.

5. The method as claimed in claim 1, wherein the palladium compound is bis(dibenzylideneacetone)palladium(0).

6. The method as claimed in claim 1, wherein the palladium compound is tris(dibenzylideneacetone)-dipalladium(0).

7. The method as claimed in claim 1, wherein the ligand is 2-(di-tert-butylphosphino)-2',4',6'-triisopropyl-1-1'-biphenyl.

8. The method as claimed in claim 1, wherein the coupling is carried out in a solvent chosen from an alcohol, an ether or an aromatic hydrocarbon.

9. The method as claimed in claim 8, wherein the solvent is dioxane.

10. The method as claimed in claim 1, wherein the basic agent is a phosphate or a carbonate.

11. The method as claimed in claim 10, wherein the basic agent is tripotassium phosphate, potassium carbonate or cesium carbonate.

12. The method as claimed in claim 1, wherein the coupling is carried out at a temperature between 60° C. and 120° C.

13. A benzofuran derivative of general formula:

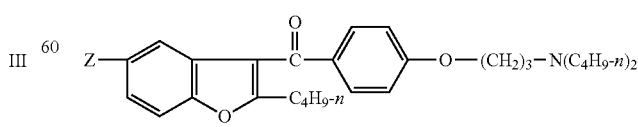

XVIII in which Z represents a halogen, the hydroxyl group or a sulfonate group of formula $—O—SO_2R_3$ in which $R_3$ represents a trifluoromethane or imidazolyl group.

14. The benzofuran derivative as claimed in claim 13, in which Z represents bromine.

15. The benzofuran derivative as claimed in claim 13, in which Z represents the hydroxyl group.

* * * * *